United States Patent
Rubin et al.

(10) Patent No.: US 10,070,682 B2
(45) Date of Patent: Sep. 11, 2018

(54) METHOD FOR MONITORING AN INDIVIDUAL'S MOTOR LOAD AND INSOLE FOR THE IMPLEMENTATION THEREOF

(71) Applicant: Healbe Corporation, Redwood City, CA (US)

(72) Inventors: Mikhail S. Rubin, St. Petersburg (RU); Igor L. Misjuchenko, St. Petersburg (RU); Oleg M. Gerasimov, Len. oblast' (RU); Evgeniy L. Sokolov, Len. oblast' (RU)

(73) Assignee: Healbe Corporation, Redwood City, CA (US)

( * ) Notice: Subject to any disclaimer, the term of this patent is extended or adjusted under 35 U.S.C. 154(b) by 342 days.

(21) Appl. No.: 14/832,002

(22) Filed: Aug. 21, 2015

(65) Prior Publication Data

US 2015/0351484 A1 Dec. 10, 2015

Related U.S. Application Data

(63) Continuation of application No. PCT/RU2014/000137, filed on Mar. 4, 2014.

(30) Foreign Application Priority Data

Mar. 5, 2013 (RU) .................................. 2013110572

(51) Int. Cl.
*A43B 3/00* (2006.01)
*A43B 5/00* (2006.01)
(Continued)

(52) U.S. Cl.
CPC .............. *A43B 3/0005* (2013.01); *A43B 5/00* (2013.01); *A61B 5/1036* (2013.01);
(Continued)

(58) Field of Classification Search
CPC ..... G01G 19/52; A61B 5/1036–5/1038; A61B 5/1118; A61B 5/6807
See application file for complete search history.

(56) References Cited

U.S. PATENT DOCUMENTS 5,885,229 A * 3/1999 Yamato ................ A61B 5/1038
600/587
5,925,001 A * 7/1999 Hoyt .................... A61B 5/1036
600/595

(Continued)

FOREIGN PATENT DOCUMENTS

EP 2556795 A1 2/2013
FR 2873281 A1 1/2006

(Continued)

OTHER PUBLICATIONS

International Search Report from International Application No. PCT/RU2014/000137, filed Mar. 4, 2014, dated Aug. 21, 2014.

(Continued)

*Primary Examiner* — Michael C Stout
(74) *Attorney, Agent, or Firm* — Patentbar International, P.C.

(57) ABSTRACT

A method for measurements of parameters characterizing human motor activity provides registration of signals generated by load sensors mounted in shoe insoles, with each insole having at least two load sensors, one mounted near the heel, and the other near the toe of the foot. The specific type of motor activity is determined based on temporal correlation of load sensor signals from both insoles and values thereof. Person's weight, including additionally carried weight, is determined by summing up signal values from said load sensors, with the specific type of motor activity considered; thereafter, person's motor stress is determined based on specified type of motor activity and person's weight, including additionally carried weight. The method (Continued)

enables a real-time monitoring of motor stress of a person at different types of motor activity, e.g. running, walking at different pace, standing, with person's weight, including additionally carried weight, taken into consideration.

6 Claims, 4 Drawing Sheets

(51) Int. Cl.
| | | |
|---|---|---|
| G01G 3/14 | (2006.01) | |
| G01G 19/44 | (2006.01) | |
| G01G 19/52 | (2006.01) | |
| A61B 5/103 | (2006.01) | |
| A61B 5/11 | (2006.01) | |
| A61B 5/00 | (2006.01) | |

(52) U.S. Cl.
CPC .......... *A61B 5/1118* (2013.01); *A61B 5/6807* (2013.01); *G01G 3/14* (2013.01); *G01G 19/44* (2013.01); *G01G 19/52* (2013.01)

(56) References Cited

U.S. PATENT DOCUMENTS

| | | | |
|---|---|---|---|
| 6,183,425 B1 | 2/2001 | Whalen et al. | |
| 8,467,979 B2* | 6/2013 | Sobolewski | A43B 1/0054 36/25 R |
| 2006/0020421 A1* | 1/2006 | Darley | A43B 3/0005 702/182 |
| 2007/0123391 A1* | 5/2007 | Shin | A43B 3/0005 482/8 |
| 2007/0202478 A1 | 8/2007 | Al-Obaidi et al. | |
| 2008/0167580 A1* | 7/2008 | Avni | A43B 3/0005 600/587 |
| 2010/0211355 A1* | 8/2010 | Horst | A61B 5/1038 702/173 |
| 2010/0305478 A1* | 12/2010 | Ordway | A61B 5/1038 600/587 |
| 2011/0054359 A1* | 3/2011 | Sazonov | A43B 3/0005 600/595 |
| 2011/0054809 A1* | 3/2011 | Templeman | A61B 5/1118 702/44 |
| 2012/0253234 A1* | 10/2012 | Yang | A61B 5/1038 600/595 |
| 2013/0190903 A1* | 7/2013 | Balakrishnan | A61B 5/7246 700/91 |
| 2014/0195023 A1* | 7/2014 | Statham | A61B 5/1038 700/91 |
| 2015/0153374 A1* | 6/2015 | Balakrishnan | G01P 13/00 702/178 |

FOREIGN PATENT DOCUMENTS

| | | |
|---|---|---|
| JP | 06-14803 A | 1/1994 |
| JP | 10-313902 A | 12/1998 |
| JP | 2002-500768 A | 1/2002 |
| KR | 100792327 B1 | 12/2007 |
| RU | 103064 U1 | 3/2011 |
| WO | 2001/035818 A2 | 5/2001 |

OTHER PUBLICATIONS

Sazonova, Nadezhda et al., Prediction of Bodyweight and Energy Expenditure Using Point Pressure and Foot Acceleration Measurements, The Open Biomedical Engineering Journal, 2011, pp. 110-115, v. 5.

Kotz, Y. M. Sports Physiology. Textbook for Institutes of Physical Education; Moscow: Physical Culture and Sport, 1998, pp. 6-9.

* cited by examiner

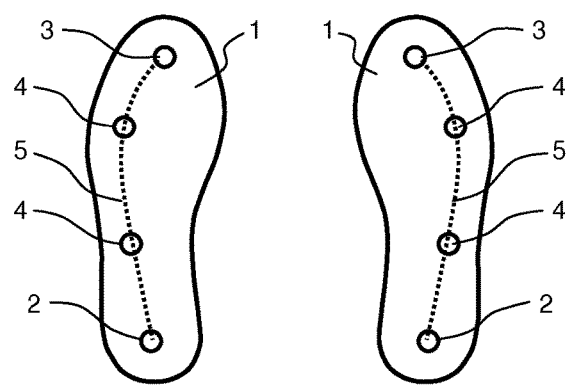
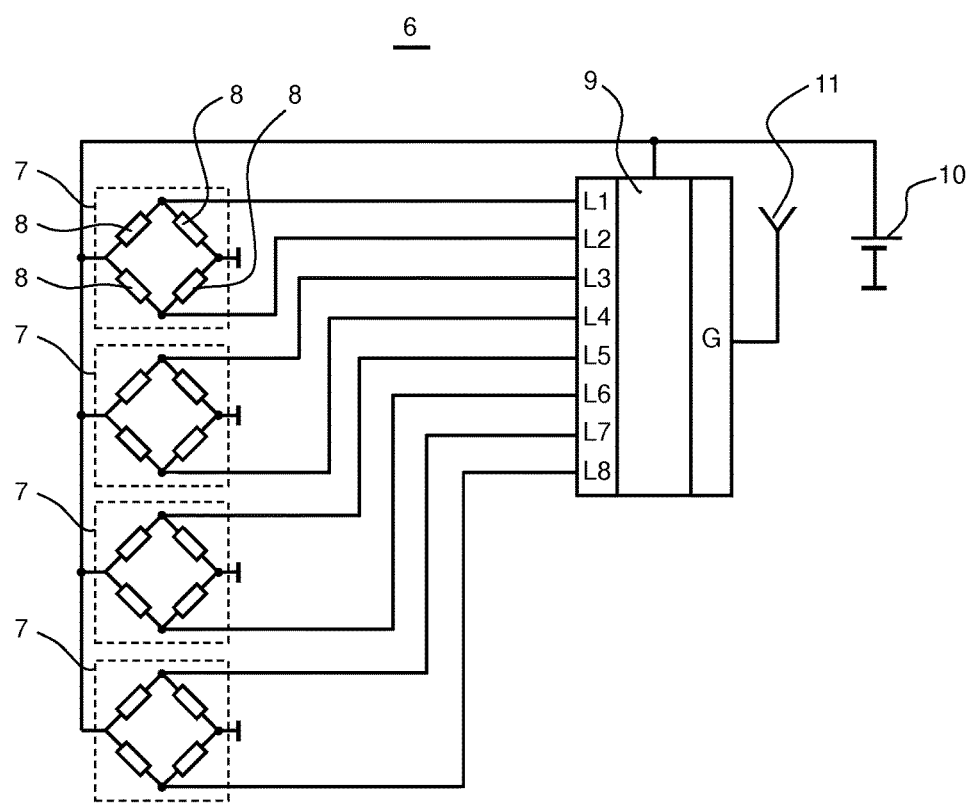
Fig. 1
Fig. 2

METHOD FOR MONITORING AN INDIVIDUAL'S MOTOR LOAD AND INSOLE FOR THE IMPLEMENTATION THEREOF

RELATED APPLICATIONS

This Application is a Continuation application of International Application PCT/RU2014/000137, filed on Mar. 4, 2014, which in turn claims priority to Russian Patent Application No. RU 2013110572, filed Mar. 5, 2013, both of which are incorporated herein by reference in their entirety.

FIELD OF INVENTION

The invention relates to the field of monitoring parameters measurements of human motor activity, in particular, to motor stress measurements using load sensors disposed in a shoe insole.

BACKGROUND OF THE INVENTION

Various methods are known for measuring human motion parameters by means of load sensors located in shoe insoles.

Patent KR 100792327 (publication date Dec. 31, 2007; IPC A43B3/00, A43B5/00), for instance, describes a method for measuring player's weight and displacement of his bodily center of gravity at golfing by means of piezoelectric sensors placed under shoe insoles. Measurements of force acting upon the sensor at golfing render it possible to obtain a real-time assessment of player's motion pattern and motion performance accuracy. However, this method provides no means for measuring human motor stress during the game.

International patent application WO 2001/035818 (publication date May 25, 2001; IPC A61B5/103) describes a method for measuring the force generated by athlete's legs at long and high jump, in games, or at leisure. The force is measured by at least one load sensor located in a shoe insole. A transceiver with antenna and a power supply are mounted in the shoe to provide the transmission of measured data to an external processing unit. However, this method does not allow for assessment of human motor stress during sporting activities based on signals from load sensors.

The concept of patent FR 2873281 (publication date Jul. 26, 2004; IPC A43B3/00, A43B5/00, A61B5/103) is the closest to the one claimed here; it describes sporting shoes having a measuring device to determine physical parameters of motion and calculate human motor stress thereby. The shoes are equipped with load sensors disposed underneath human foot, and a computing unit with display for showing the information related to human motor stress. Measurements of physical parameters by such a device allow a person's walking pattern to be identified; whereat said parameters include: pace, velocity, acceleration, distance covered, travel time, rate of bodily metabolism and other parameters related to energy consumption, such as total amount of energy burned by the person. This enables a general monitoring of human motor stress. However, such an evaluation of motor stress ignores additional motor weight, i.e. weight carried at walking, running or other type of motor activity, which is generally a variable value throughout the period of monitoring. All the above leads to incorrect assessments of motor stress or restricts the applicability of this method. Furthermore, this method enables measurements of only walking stress and cannot be applied to other types of motor activity, for example running.

The technical problem to be solved by the present invention is the development of a method to assess human motor stress in real time, with person's body weight, including additionally carried weight, taken into account; said method being applicable to various types of motor activity, such as running, walking at various pace, as well as standing.

SUMMARY OF THE INVENTION

One of the objects of the present invention is a method of monitoring motor stress of a person, wherein signals generated by load sensors mounted in shoe insoles are registered; whereat each insole has two load sensors: a first load sensor being disposed in the heel region and the second sensor being disposed in the toe region of the foot. The specific type of motor activity is identified based on correspondence in time of load sensor signals from both insoles and the values of the signals. The weight of the human, as well as additionally carried weight, is determined by summing up the load sensor signals and by the type of the determined motor activity. Thereafter, the motor stress is determined based on the type of motor activity and the body weight, including additionally carried weight.

When running or walking, a human moves feet alternately, first one, then the other. The load sensors located in the heel region and in the toe region make it possible to determine the duration of the foot's contact with the base (support phase) and the duration of stride (stride phase) within one walking or running cycle. Since different types of motor activities are characterized by different correspondence in time of the support time and the stride time, that correspondence in time (temporal correlation) of load sensor signals from different insoles permits to determine the pattern or the type of motor activity that needs to be identified.

The inventive method provides for the determination of the motor stress of a human based on both the type of motor activity (walking, running, etc.) and the weight of the human, including additionally carried weight. The weight plus the additionally carried weights are measured directly in the process of the motor activity. Thus, the motor stress of the human in a particular situation can be measured much more accurately, and monitoring that stress can be performed more effectively over a specified time period.

In particular embodiments of this method, identification of various types of motor activity becomes feasible according to the procedure described below.

Such type of motor activity as walking is determined if the values of the signals from the load sensors in both insoles exhibit periodic variations of the values of the signals, and the signals from the load sensors from different insoles partially overlap in time.

Such type of motor activity as running is determined if the values of the signals from the load sensors in both insoles exhibit periodic variations of the values of the signals, and the signals from the load sensors from different insoles do not overlap in time.

Such type of motor activity as standing is determined if the values of the signals from the load sensors in both insoles exhibit periodic variations of the values of the signals, and the signals from the load sensors from different insoles overlap in time.

The inventors have obtained a series of empirical relationships that permit to determine the weight of a human, including additionally carried weight, with the specific type of motor activity taken into account.

For example, weight P, including additionally carried weight, of a human who is walking at a slow pace of 60 steps per minute can be determined as follows:

$$P = K_W \cdot F,$$

where:

$K_W$ is a calibration factor determined for a specific person with a known weight at walking;

F is the mean value of a foot pressure force over one walking cycle, wherein:

$$F = (F_{1max} + F_{2max})/2,$$

where:

$F_{1max}$ is the maximum value of summarized foot pressure forces registered by all load sensors of one insole;

$F_{2max}$ is the maximum value of summarized foot pressure forces registered by all load sensors of the other insole, wherein one cycle consists of two consecutive steps made by one foot and then the other.

The weight, including additionally carried weight, of a human who is walking at a pace of 60 or more steps per minute can be determined as follows:

$$P = K_W \cdot F \cdot (1010 - 1.2 \cdot V - 0.026 \cdot V^2) \cdot 0.001,$$

where:

$K_W$ is a calibration factor for a given person with a known weight who is walking at a pace of up to 60 steps per minute;

F is the mean value of a foot pressure force over one walking cycle, wherein:

$$F = (F_{1max} + F_{2max})/2,$$

where:

$F_{1max}$ is the maximum value of summarized foot pressure forces registered by all load sensors of one insole;

$F_{2max}$ is the maximum value of summarized foot pressure forces registered by all load sensors of the other insole;

V is the number of steps per minute, wherein one cycle consists of two consecutive steps made by one foot and then the other.

The weight, including additionally carried weight, of a running human can be determined by formula:

$$P = K_R \cdot F \cdot (1090 - 4.4 \cdot V - 0.045 \cdot V^2) \cdot 0.001,$$

where:

$K_R$ is a calibration factor for a given person with the known weight at running;

F is the mean value of a foot pressure force over one running cycle, wherein:

$$F = (F_{1max} + F_{2max})/2,$$

where:

$F_{1max}$ is the maximum value of summarized foot pressure forces registered by all load sensors of one insole;

$F_{2max}$ is the maximum value of summarized foot pressure forces registered by all load sensors of the other insole;

V is the number of steps per minute, wherein one running cycle consists of two consecutive steps made by one foot and then the other.

The weight, including additionally carried weight, of a standing human can be determined by formula:

$$P = K_S \cdot F,$$

where:

$K_S$ is a calibration factor to be determined for a given human with a known weight at standing;

F is the mean value of foot pressure force over the period of standing, wherein:

$$F = (F_{1max} + F_{2max})/2,$$

where:

$F_{1max}$ is the maximum value of summarized foot pressure forces registered by all load sensors of one insole;

$F_{2max}$ is the maximum value of summarized foot pressure forces registered by all load sensors of the other insole;

In particular, the motor stress at walking $E_W$ can be determined by formula:

$$E_W = e_W \sum_{i=1}^{w} P_i \cdot T_i,$$

where:

i is the number of time interval committed to walking activity;

w is the number of time intervals committed to walking activity;

$P_i$ is the weight of the human, including additionally carried weight, (in kg) registered within i-th time interval;

$T_i$ is the duration of i-th time interval (in min.);

$e_W$ is specific energy input to walking activity, in kcal per kg of weight per minute, expressed as follows:

$$e_W = k_{per} \cdot (25 - 0.13 \cdot V + 0.022 \cdot V^2 + 0.00038 \cdot V^3 + 0.0000021 \cdot V^4),$$

where:

$k_{per}$ is an individual factor for a given person/human, to be determined in advance;

V is a number of steps per minute.

In particular, the motor stress at running $E_R$ can be calculated by formula:

$$E_R = e_R \sum_{i=1}^{r} P_i \cdot T_i,$$

where:

i is the number of time interval committed to running activity;

r is the number of time intervals committed to running activity;

$P_i$ is the weight of the human, including additionally carried weight, (in kg) registered within i-th time interval;

$T_i$ is the duration of i-th time interval (in min.);

$e_R$ is specific energy input to running activity, in kcal per kg of weight per minute, determined as follows:

$$e_R = k_{per} \cdot (73 - 2.2 \cdot V + 0.051 \cdot V^2 + 0.000335 \cdot V^3 + 0.00000077 \cdot V^4),$$

where:

$k_{per}$ is an individual factor for a given person, to be determined in advance;

V is a number of steps per minute.

In particular, the motor stress at standing $E_S$ can be determined by formula:

$$E_S = e_S \sum_{i=1}^{s} P_i \cdot T_i,$$

where:

i is the number of time interval committed to standing activity;

s is the number of time intervals committed to standing activity;

$P_i$ is the weight of the person, including additionally carried weight, (in kg) registered within i-th time interval;

$T_i$ is the duration of i-th time interval (in min.);

$e_S$ is specific energy input to standing activity, in kcal per kg of weight per minute, determined as follows:

$$e_S = k_{per} \cdot 25,$$

$k_{per}$ is an individual factor for a given person, to be determined in advance;

In a particular embodiment of the method, in addition to the signals of the first and second load sensors, signals from additional load sensors disposed in each insole along the trajectory of a support reaction force at walking between the first load sensor and the second load sensor are detected. The signals from the additional sensors used for calculations together with the signals from the first and second load sensors. This allows a more accurate measurement of the weight of a human, as well as additionally carried weight.

Another object of the present invention is an insole designed for implementing the described method. The insole comprises at least a first load sensor mounted near the heel of the foot and a second load sensor mounted near the toe of the foot, both capable of generating signals that register the pressure force applied by the foot of human.

Additionally, the insole may be equipped, at least, with an analog-to-digital converter and transceiver to convert the signals from load sensors to digital form and transmit them to an external processing unit.

BRIEF DESCRIPTION OF THE DRAWINGS

The invention is illustrated by the following drawing figures:

FIG. 1 is a schematic illustration of the design of the insole with load sensors mounted therein; shown here are both, left and right insoles and location of load sensors relative to the trajectory of support reaction force at walking.

FIG. 2 is a wiring diagram of an exemplary measuring device for registering the force applied by foot upon load sensors mounted in insoles, as shown in FIG. 1—each load sensor constitutes a strain transducer with four bridge-connected strain gages.

DETAILED DESCRIPTION OF THE PREFERRED EMBODIMENTS

Figure 3:
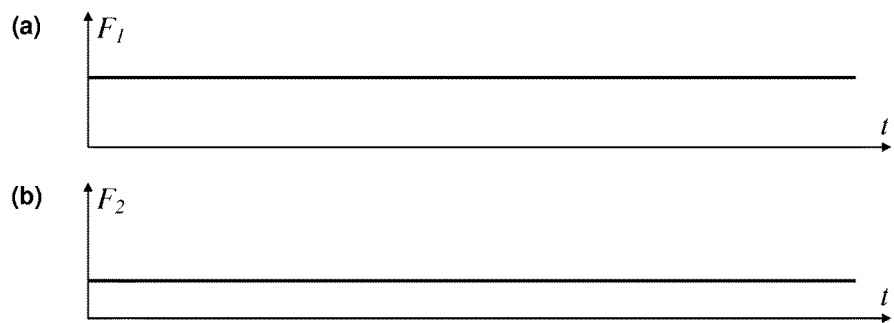
FIG. 3 shows exemplary timing diagrams which illustrate the temporal relationship of load sensor signals from both insoles as registered by the circuit shown in FIG. 2 at standing activity.

The present invention is illustrated by the following embodiments of insoles with load sensors in the form of strain gages and piezoelectric transducers.

In the first embodiment, each insole 1 (see. FIG. 1) includes a first load sensor 2 located in the heel region of the foot, a second load sensor 3 located in the toe region of the foot, and two additional load sensors 4 located actually on the trajectory 5 of support reaction force at walking. FIG. 2 shows an embodiment of a schematic diagram of device 6 for registering the force applied upon load sensor by foot. In this embodiment, load sensors 2-4 are represented by strain transducers (strain gauges) 7, each consisting of four bridge-connected strain gages 8. One bridge diagonal is connected to power supply 10, while the other is connected to input/output ports of microcontroller 9 in such a way that all four strain transducers 7 (first load sensor 2, second load sensor 3, and two additional load sensors 4) are eventually connected to eight input/output ports L1-L8 of microcontroller 9 which registers analog signals from strain transducers 7 and converts said signals to digital form. Antenna output G of microcontroller 9 with a built-in transceiver is connected to antenna 11. Device 6 is energized by power supply 10. Microcontroller 9 is switched on by commands from an external computer (not shown in the drawings). The external computer is mounted in a man-portable device and is capable of determining motor stress.

The method of motor stress monitoring according to the present invention is implemented as follows.

The type of motor activity is determined based on signals from strain gages 7 (load sensors 2-4) of both insoles 1 registered by signal processing unit 6 and time relationship of signals from strain gages 7 on left and right insoles 1.

For example, such activity as standing is distinguished by signals shown in FIG. 3, where graph (a) corresponds to signal $F_1$ from strain gage 7 of insole 1, while graph (b) corresponds to signal $F_2$ from strain gage 7 of the other insole 1. At this type of motor activity signals $F_1$ and $F_2$ from strain gages 7 of both insoles 1 are essentially equal in value and feature almost complete overlap in time. FIG. 3 shows that signal $F_1$ from strain gage 7 of insole 1 (graph (a)) is greater in value than signal $F_2$ from strain gage 7 of the other insole 1 (graph (b)). It means the person is standing leaning on one leg more than the other.

Figure 4:
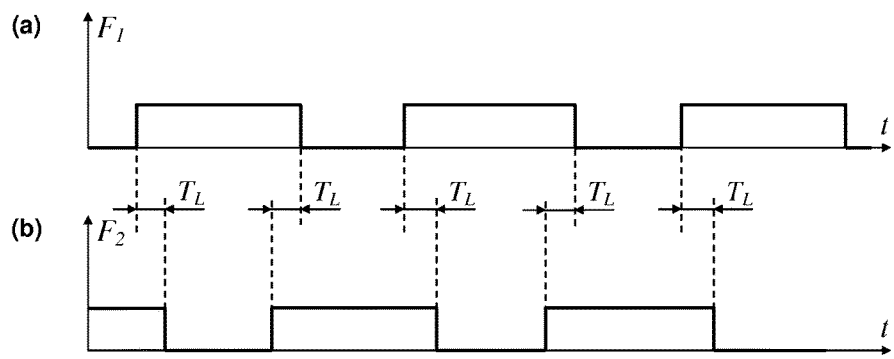
FIG. 4 shows exemplary timing diagrams which illustrate the temporal relationship of load sensor signals from both insoles as registered by the circuit shown in FIG. 2 at walking activity.

Such type of motor activity as walking is distinguished by signals shown in FIG. 4, where graph (a) corresponds to signal $F_1$ from strain gage 7 of insole 1, while graph (b) corresponds to signal $F_2$ from strain gage 7 of the other insole 1. This type of motor activity is characterized by alternating changes in signal values $F_1$ and $F_2$ from strain gages 7 of both insoles 1 and by availability of partial overlap in time (overlap time interval $T_L$).

Figure 5:
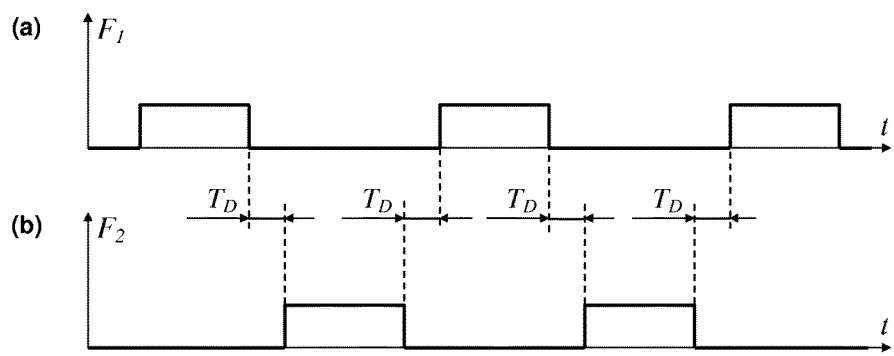
FIG. 5 shows exemplary timing diagrams which illustrate the temporal relationship of load sensor signals from both insoles as registered by the circuit shown in FIG. 2 at running activity.

Such type of motor activity as running is distinguished by signals shown in FIG. 5, where graph (a) corresponds to signal $F_1$ from strain gage 7 of insole 1, while graph (b) corresponds to signal $F_2$ from strain gage 7 of the other insole 1. This type of motor activity is characterized by alternating changes in signal values $F_1$ and $F_2$ from strain gages 7 of both insoles 1 and by absence of time overlap of said signals. Conversely, a time gap designated as time interval $T_D$ is observed between said signals.

The availability of at least two load sensors in each insole: first sensor 2 near the heel and second sensor 3 near the toe, makes it possible to define not only the above-mentioned types of motor activity (walking, running, standing), but also other types of activity like sitting, cycling, skiing. However, this method covers only those types of motor activity, in which person's weight, including additionally carried weight, is transmitted to his/her feet.

Table 1 below matches values of load sensor signals and their temporal relationship to a certain type of motor activity (with at least two sensors in one insole).

TABLE 1

| Load sensor signal values from both insoles and their temporal relationship | Type of human motor activity |
|---|---|
| Not available | Sitting, lying, with shoes removed |
| Essentially invariable values and almost complete time overlap | Standing |
| Partial overlap at cyclic repetition | Walking |
| No overlap at cyclic repetition | Running |
| Cyclic and essentially simultaneous variation of sensor signal values from both insoles | Jumping |

Similar signals from load sensors 2, 3, and 4 used to determine (identify) the type of person's motor activity can be also used to measure person's weight, including additionally carried weight. The term "additionally carried weight" means extra weight borne by a person, e.g., carried items or special training weights. At that, person's weight must be determined in advance, because the method according to the present invention involves human motor stress monitoring which requires that both the type of motor activity and person's weight, including the weight additionally carried during this activity, be taken into consideration.

The mathematical relationships related to types of motor activity that were empirically obtained by the inventors can be used for measuring person's weight, including additionally carried weight.

Thus, at standing activity the weight measurement is reduced basically to the summation of signal values from all load sensors 2-4 of both insoles.

Person's weight, including additionally carried weight, at standing can be expressed as follows:

$$P = K_S \cdot F,$$

where:
$K_S$ is a calibration factor to be determined for a given person with a known weight at standing;
F is the mean value of pressure force of feet at standing. It can be determined for a certain period of time, e.g., from 5 to 10 seconds, wherein:

$$F = (F_{1max} + F_{2max})/2,$$

where:
$F_{1max}$ is the maximum value of summarized foot pressure forces registered by all load sensors of one insole;
$F_{2max}$ is the maximum value of summarized foot pressure forces registered by all load sensors of the other insole;
Calibration factor $K_S$, as well as other calibration factors used in calculations of person's weight at walking or running, can be determined in the process of system calibration. At the same time, they can also be determined directly during monitoring, when the person is known to carry no additional weight at this point in time, i.e., load sensors take up only person's known sole weight.

At slow walking pace of up to 60 steps per minute, person's weight P, including additionally carried weight, can be calculated using formula:

$$P = K_W \cdot F,$$

where:
$K_W$ is a calibration factor to be determined for a walking person with known weight;
F is the mean value of foot pressure force over one walking cycle, wherein:

$$F = (F_{1max} + F_{2max})/2,$$

where:
$F_{1max}$ is the maximum value of summarized foot pressure forces registered by all load sensors of one insole;
$F_{2max}$ is the maximum value of summarized foot pressure forces registered by all load sensors of the other insole,
whereat one cycle is assumed to consist of two consecutive steps made by one foot and the other.

At walking pace of 60 or more steps per minute, person's weight, including additionally carried weight, can be found by formula:

$$P = K_W \cdot F \cdot (1010 - 1.2 \cdot V - 0.026 \cdot V^2) \cdot 0.001,$$

where:
$K_W$ is a calibration factor to be determined for a given person with known weight, who is walking at pace of up to 60 steps per minute;
F is the mean value of foot pressure force over one walking cycle, wherein:

$$F = (F_{1max} + F_{2max})/2,$$

where:
$F_{1max}$ is the maximum value of summarized foot pressure forces registered by all load sensors of one insole;
$F_{2max}$ is the maximum value of summarized foot pressure forces registered by all load sensors of the other insole;
V is the number of steps per minute,
whereat a cycle is assumed to consist of two consecutive steps with one foot and the other.

The weight, including additionally carried weight, of a person at running can be determined by formula:

$$P = K_R \cdot F \cdot (1090 - 4.4 \cdot V - 0.045 \cdot V^2) \cdot 0.001,$$

where:
$K_R$ is a calibration factor, which is determined for a given person with known weight at running;
F is the mean value of foot pressure force over one running cycle, wherein:

$$F = (F_{1max} + F_{2max})/2,$$

where:
$F_{1max}$ is the maximum value of summarized foot pressure forces registered by all load sensors of one insole;
$F_{2max}$ is the maximum value of summarized foot pressure forces registered by all load sensors of the other insole;
V is the number of steps per minute at a given running pace,
whereat one running cycle is assumed to consist of two consecutive steps made by one foot and the other.

The motor stress, with type of motor activity and person's weight, including additionally carried weight, considered, is determined as follows.

Motor stress at walking $E_W$ is found by formula:

$$E_W = e_W \sum_{i=1}^{w} P_i \cdot T_i,$$

where:
i is the serial number of time interval committed to walking activity;

w is the number of time intervals committed to walking activity;

$P_i$ is person's weight, including additionally carried weight, registered within i-th time interval (in kg);

$T_i$ is duration of i-th time interval (in min);

$e_S$ is specific energy input to walking activity, in kcal per kg of weight per minute, determined as follows:

$$e_W = k_{per} \cdot (25 - 0.13 \cdot V + 0.022 \cdot V^2 + 0.00038 \cdot V^3 + 0.0000021 \cdot V^4),$$

where:

$k_{per}$ is an individual factor for a given person, to be determined in advance;

V is the number of steps per minute at a given walking pace.

Factor $k_{per}$ can be determined, for example, as described in: Kotz, Y. M. *Sports Physiology*. Moscow: Physical Culture and Sport, 1998, p. 69, and can range from 0.6 to 1.1. The values that $k_{per}$ can take for people of different age are shown in Table 2 below.

TABLE 2

|  | 20-29 years | 30-39 years | 40-49 years | 50-59 years | over 60 years |
|---|---|---|---|---|---|
| For males | 1.07 | 1.0 | 0.93 | 0.82 | 0.64 |
| For females | 0.94 | 0.81 | 0.77 | 0.68 | 0.61 |

Motor stress of a person at running $E_R$ is as follows:

$$E_R = e_R \sum_{i=1}^{r} P_i \cdot T_i,$$

where:

i is the serial number of time interval committed to running activity;

r is the number of time intervals committed to running activity;

$P_i$ is person's weight, including additionally carried weight, (in kg) registered within i-th time interval;

$T_i$ is duration of i-th time interval (in min);

$e_R$ is specific energy input to running activity, in kcal per kg of weight per minute, determined as follows:

$$e_R = k_{per} \cdot (73 - 2.2 \cdot V + 0.051 \cdot V^2 + 0.000335 \cdot V^3 + 0.00000077 \cdot V^4),$$

where:

$k_{per}$ is an individual factor for a given person, to be determined in advance;

V is the number of steps per minute at a given running pace.

Figure 6:
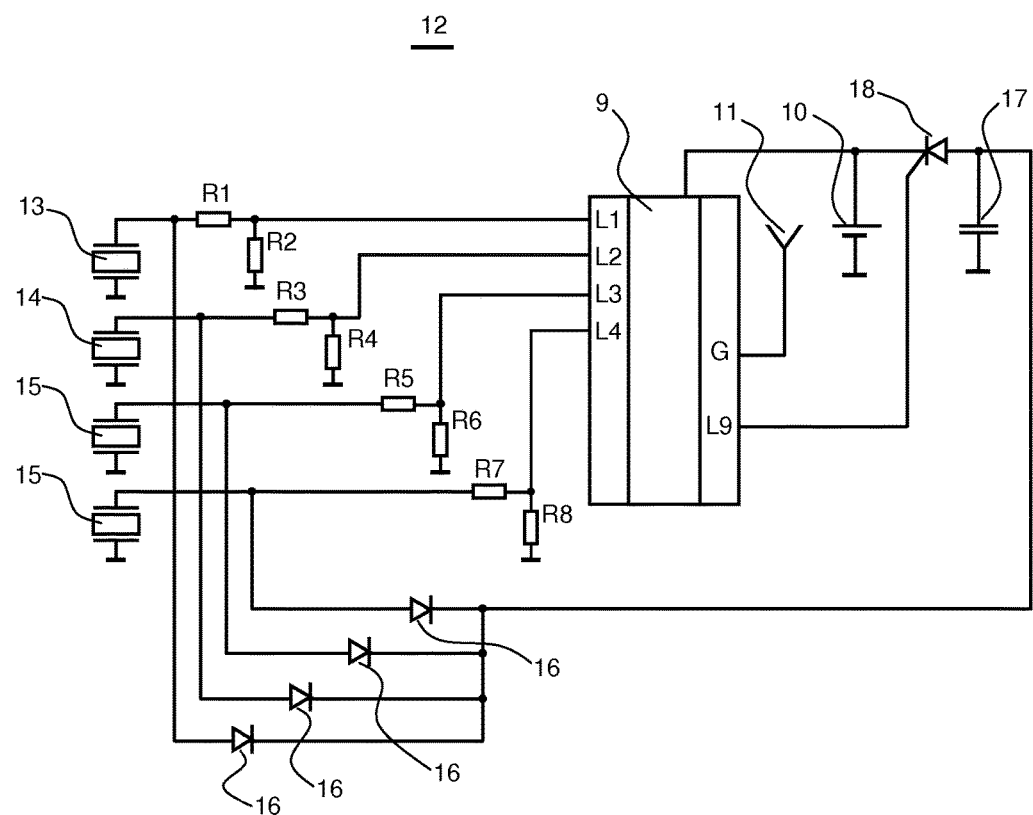
FIG. 6 shows a circuit diagram of another exemplary measuring device for registering the force applied by foot upon load sensors placed in insole, as shown in FIG. 1. In this embodiment, each load sensor constitutes a piezoelectric transducer.

Motor stress of a person at standing $E_S$ can be expressed as:

$$E_S = e_S \sum_{i=1}^{s} P_i \cdot T_i,$$

where:

i is the serial number of time interval committed to standing activity;

s is the number of time intervals committed to standing activity;

$P_i$ is person's weight, including additionally carried weight, (in kg) registered within i-th time interval;

$T_i$ is duration of i-th time interval (in min);

$e_S$ is specific energy input to standing activity, in kcal per kg of weight per minute, determined as follows:

$$e_S = k_{per} \cdot 25,$$

where $k_{per}$ is an individual factor for a given person, to be determined in advance;

Another embodiment of device 12 for implementing this method using piezoelectric transducers as load sensors is shown in FIG. 6. Similarly to the preceding embodiment, right and left insoles 1 (see FIG. 1) include first load sensor 2 located near the heel, second load sensor 3 located near the toe, and two additional sensors 4 located essentially along the trajectory 5 of support reaction force at walking. Load sensors 2, 3, and 4 in this embodiment consist of piezoelectric transducers 13, 14, and 15, respectively, connected via matching resistors R1-R8 to input/output ports L1-L4 of microcontroller 9. Similarly to the embodiment shown in FIG. 2, antenna output G of microcontroller 9 is connected to antenna 11.

The method of motor stress monitoring based on the use of piezoelectric transducers as load sensors is implemented as follows.

Figure 7:
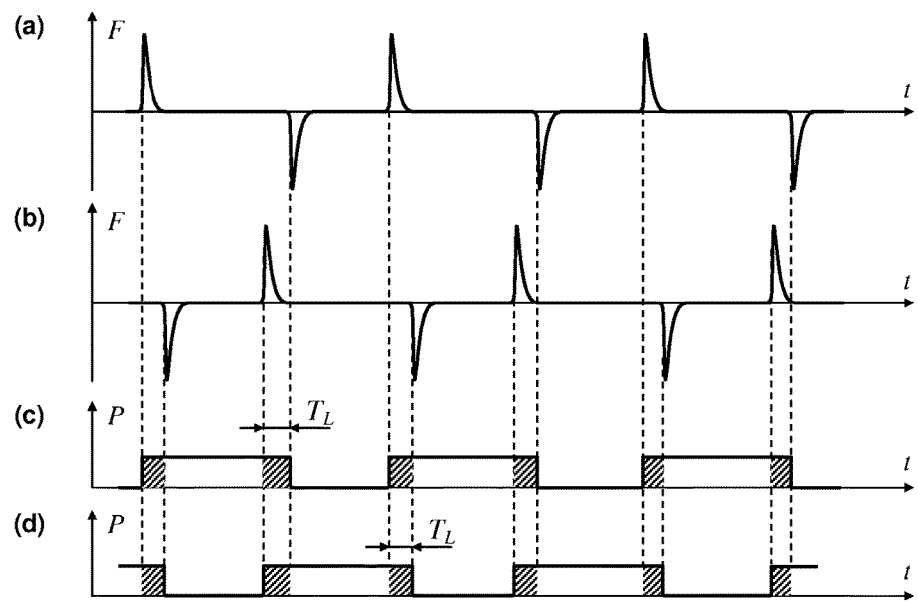
FIG. 7 shows exemplary timing diagrams which illustrate the temporal relationship of load sensor signals from both insoles as registered by the circuit shown in FIG. 6 at walking activity.
Figure 8:
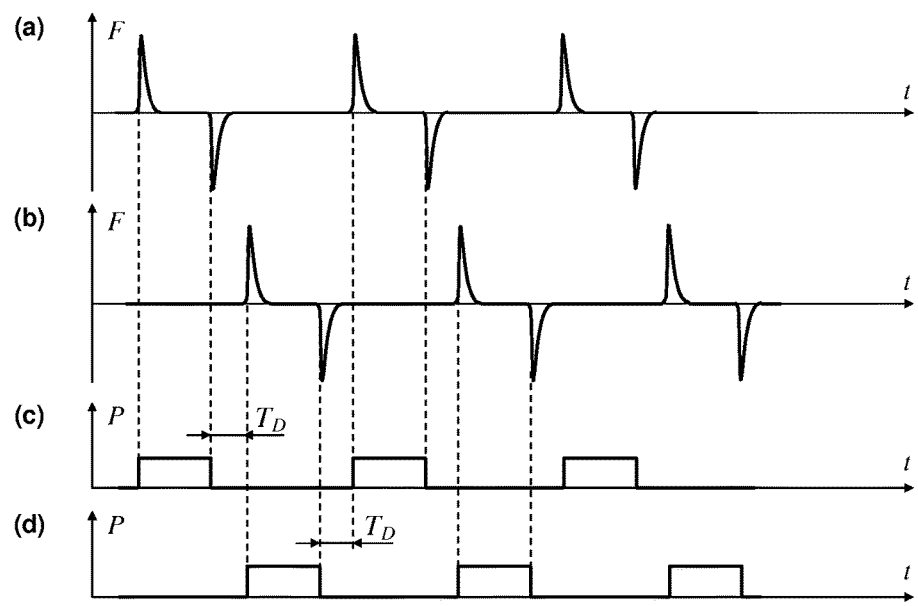
FIG. 8 shows exemplary timing diagrams which illustrate the temporal relationship of load sensor signals from both insoles as registered by the circuit shown in FIG. 6 at running activity.

Similarly to the first embodiment of the inventive method, signals from load sensors 2, 3, and 4 of each insole 1 represented here by piezoelectric transducers 13, 14, and 15, respectively, are registered. FIG. 7 shows exemplary timing diagrams which illustrate the temporal relationship of load sensor signals (e.g., piezoelectric transducers 13) from both insoles at walking, whereas FIG. 8 shows the same at running Contrary to the embodiment with strain transducers 7 (see FIG. 4 and FIG. 5), signals from the piezoelectric transducers, given their inherent amplitude-frequency response, are shaped as distinctive spikes corresponding to the moment the foot pressure is applied to piezoelectric transducer and released from said transducer (a signal of reverse polarity). The availability of spikes with opposing polarities makes it possible to reconstruct the signal corresponding to the duration of support phase, and, similarly to the preceding example, determine temporary relationships of signals from piezoelectric transducers of both insoles.

Thus, such type of motor activity as walking is characterized by signals shown in FIG. 7, where graph (a) corresponds to signal $F_1$ from piezoelectric transducer 13 (also known as sensor 2) of one insole 1, and graph (b) corresponds to signal $F_2$ from piezoelectric transducer 13 (also known as sensor 2) of the other insole 1. Graphs (c) and (d) in FIG. 7 show signals $P_1$ and $P_2$ corresponding to the duration of foot pressure on piezoelectric transducers 13 of one insole and other insole 1, respectively. The rising edge of signals $P_1$ and $P_2$ in graphs (c) and (d) of FIG. 7 correlates with signals $F_1$ and $F_2$ of positive polarity in graphs (a) and (b) of FIG. 7, respectively, while the falling edge of signals $P_1$ and $P_2$ in graphs (c) and (d) of FIG. 7 correlates with signals $F_1$ and $F_2$ of negative polarity in graphs (a) and (b) of FIG. 7, respectively. Such type of motion activity as walking is characterized by alternating variation of signal values shown in graphs (c) and (d), and by availability of their partial overlap (overlap time interval $T_L$).

Similarly, such type of motor activity as running is characterized by signals shown in FIG. 8, where graph (a) corresponds to signal $F_1$ from piezoelectric transducer 13 (also known as sensor 2) of one insole 1, and graph (b) corresponds to signal $F_2$ from piezoelectric transducer 13 (also known as sensor 2) of the other insole 1. Graphs (c) and (d) in FIG. 8 show signals $P_1$ and $P_2$ corresponding to the duration of foot pressure on piezoelectric transducers 13 of one insole and other insole 1, respectively. The rising edge of signals $P_1$ and $P_2$ in graphs (c) and (d) of FIG. 8 correlates with signals $F_1$ and $F_2$ of positive polarity in graphs (a) and (b) of FIG. 8, respectively, while the falling edge of signals $P_1$ and $P_2$ in graphs (c) and (d) of FIG. 8 correlates with signals $F_1$ and $F_2$ of negative polarity in graphs (a) and (b) of FIG. 8, respectively. Such type of motion activity as running is characterized by alternating variation of signal values shown in graphs (c) and (d) with no overlap in time. Conversely, a time gap designated as time interval $T_D$ between these signals is observed.

To measure person's weight, including additionally carried weight, the mathematical relations from the first embodiment of the present invention can be applied. In this case, maximum values of signals $F_1$ и $F_2$ from piezoelectric transducers are used to represent the pressure force exerted by foot on load sensors located in insoles. In case of standing, person's weight is determined based on the values of signals $F_1$ and $F_2$ generated by piezoelectric transducers at the beginning of standing activity and after its termination. Apart from that, the implementation of the method is similar to the one described in the preceding example.

Devices 6 (FIG. 2) and 12 (FIG. 6), as well as portions thereof, can be accommodated in insole 1 alongside with corresponding load sensors. The devices are energized by battery 10 which can be represented by a rechargeable battery. Additionally, the device can comprise a circuit for battery recharging while walking or running, as shown in the example of device 12 (see FIG. 6). Such a recharging circuit includes diodes 16, one for each piezoelectric transducer 13-15, storage capacitor 17, and thyristor 18 whose control input is coupled to input/output port L9 of microcontroller 9. One end of each diode 16 is connected to corresponding piezoelectric transducer 13-15, while all other ends are joined and connected to capacitor 17. In the process of recharging, microcontroller 9 switches off the registration mode of signals generated by foot pressure on piezoelectric transducers, sending said signals through diodes 16 to storage capacitor 17. In this mode, microcontroller 9 opens thyristor 18, thereby connecting charged capacitor 17 to battery 10. Thus, when a person is walking or running in shoes with device 12 and piezoelectric transducers 13-15 mounted in shoe insoles, battery 10 is recharged.

The method according to the present invention enables a more accurate assessment of type and duration of human motor activity and a more precise calculation of person's motor stress throughout the day, with the type of motor activity and person's weight, including additionally carried weight, taken into account.

Moreover, the data registered by load sensors mounted in insoles, as described above, may also be used to detect the defects of person's musculoskeletal system, flat footedness, as well as to determine the slope of travel surface and its hardness, degree of comfort of footwear worn, identification of gait specific for a person, etc. The method also enables a continuous monitoring of traveling pace, motion speed and acceleration, covered distance, and duration of travel.

What is claimed is:

1. A method of determining weight of a person and additional weight carried by the person walking at a pace of up to 60 steps per minute, comprising:

providing the person with shoes each having (i) a first load sensor disposed in a heel region of a shoe insole and (ii) a second load sensor disposed in a toe region of the shoe insole;

registering signals from the first and second load sensors; and using the signals to determine the weight and the additional weight as follows:

$$P=K_W \cdot F,$$

wherein:

$K_W$ is a calibration factor determined for a person of known weight walking at a pace of up to 60 steps per minute;

F is a mean value of a foot pressure force over one walking cycle, wherein:

$$F=(F_{1max}+F_{2max})/2,$$

where:

$F_{1max}$ is a maximum value of summarized foot pressure forces registered by the first and second load sensors in one insole; and $F_{2max}$ is a maximum value of summarized foot pressure forces registered by all the first and second load sensors in other insole;

wherein the walking cycle consists of two consecutive steps made by the person.

2. A method of determining weight of a person and additional weight carried by the person walking at a pace of 60 or more steps per minute, comprising:

providing the person with shoes each having (i) a first load sensor beings disposed in a heel region of a shoe insole and (ii) a second load sensor being disposed in a toe region of the shoe insole;

registering signals from the first and second load sensors; and using the signals to determine the weight and the additional weight as follows:

$$P=K_W \cdot F \cdot (1010-1.2 \cdot V-0.026 \cdot V^2) \cdot 0.001,$$

wherein:

$K_W$ is a calibration factor determined for a person of known weight walking at a pace of up to 60 steps per minute;

F is a mean value of foot pressure force over one walking cycle, wherein:

$$F=(F_{1max}+F_{2max})/2,$$

where:

$F_{1max}$ is a maximum value of summarized foot pressure forces registered by all the load sensors of one insole;

$F_{2max}$ is the maximum value of summarized foot pressure forces registered by the first and second load sensors in other insole; and V is a number of steps of the person per minute;

wherein the walking cycle consists of two consecutive steps made by the person.

3. A method of determining weight of a person and additional weight carried by the person during running, comprising:

providing the person with shoes each having (i) a first load sensor disposed in a heel region of a shoe insole and (ii) a second load sensor disposed in a toe region of the shoe insole registering signals from the first and second load sensors; and using the signals to determine the weight and the additional weight as follows:

$$P=K_R \cdot F \cdot (1090-4.4 \cdot V-0.045 \cdot V^2) \cdot 0.001,$$

wherein:

$K_R$ is a calibration factor determined for a person of known weight at running;

F is a mean value of a foot pressure force over one running cycle, wherein:

$$F=(F_{1max}+F_{2max})/2,$$

wherein:
- $F_{1max}$ is a maximum value of summarized foot pressure forces registered by the first and second load sensors of one insole;
- $F_{2max}$ is the maximum value of summarized foot pressure forces registered by the first and second load sensors in other insole; and
- V is a number of steps of the person per minute;

wherein the running cycle consists of two consecutive steps made by the person.

4. A method of determining motion stress of a person at walking, comprising:
   providing the person with shoes each having a first load sensor beings disposed in a heel region of a shoe insole and a second load sensor being disposed in a toe region of the shoe insole;
   registering signals from the first and second load sensors; and
   using the signals to determine the motion stress at walking as follows:

$$E_W = e_W \sum_{i=1}^{w} P_i \cdot T_i,$$

wherein:
- i is a number of a walking time interval;
- w is a number of walking time intervals;
- $P_i$ is weight of the person, including additional weight carried by the person, in kilograms, registered within an i-th time interval;
- $T_i$ is a duration of the i-th time interval in minutes;
- $e_W$ is a specific energy input, in kcal per kg of weight per minute, determined as follows:

$$e_W=k_{per}\cdot(25-0.13\cdot V+0.022\cdot V^2+0.00038\cdot V^3+0.0000021\cdot V^4),$$

wherein:
- $k_{per}$ is a predetermined factor for the person; and
- V is a number of steps of the person per minute.

5. A method of determining motion stress of a person at running, comprising:
   providing the person with shoes each having a first load sensor beings disposed in a heel region of a shoe insole and a second load sensor being disposed in a toe region of the shoe insole;
   registering signals from the first and second load sensors; and
   using the signals to determine the motion stress at running as follows:

$$E_R = e_R \sum_{i=1}^{r} P_i \cdot T_i,$$

wherein:
- i is a number of a walking time interval;
- w is a number of walking time intervals;
- $P_i$ is weight of the person, including additional weight carried by the person, in kilograms, registered within an i-th time interval;
- $T_i$ is a duration of the i-th time interval in minutes;
- $e_R$ is a specific energy input, in kcal per kg of weight per minute, determined as follows:

$$e_R=k_{per}\cdot(73-2.2\cdot V+0.051\cdot V^2+0.000335\cdot V^3+0.00000077\cdot V^4),$$

wherein:
- $k_{per}$ is a predetermined factor for the person; and
- V is a number of steps of the person per minute.

6. A method of determining motion stress of a person at standing, comprising:
   providing the person with shoes each having a first load sensor beings disposed in a heel region of a shoe insole and a second load sensor being disposed in a toe region of the shoe insole;
   registering signals from the first and second load sensors; and
   using the signals to determine the motion stress at standing as follows:

$$E_S = e_S \sum_{i=1}^{s} P_i \cdot T_i,$$

wherein:
- i is a number of a walking time interval;
- w is a number of walking time intervals;
- $P_i$ is weight of the person, including additional weight carried by the person, in kilograms, registered within an i-th time interval;
- $T_i$ is a duration of the i-th time interval in minutes;
- $e_S$ is a specific energy input, in kcal per kg of weight per minute, determined as follows:

$$e_S=k_{per}\cdot 25,$$

wherein $k_{per}$ is a predetermined individual factor for the person.

* * * * *